(12) United States Patent
Betz

(10) Patent No.: US 6,501,821 B2
(45) Date of Patent: Dec. 31, 2002

(54) MEDICAL DEVICE HAVING AN ARRANGEMENT FOR TRANSMITTING DATA FROM A DATA GENERATING UNIT TO A RELATIVELY DISPLACEABLE DATA PROCESSING UNIT

(75) Inventor: Roland Betz, Viereth-Trunstadt (DE)

(73) Assignee: Siemens Aktiengesellschaft, Munich (DE)

( * ) Notice: Subject to any disclaimer, the term of this patent is extended or adjusted under 35 U.S.C. 154(b) by 58 days.

(21) Appl. No.: 09/784,580

(22) Filed: Feb. 15, 2001

(65) Prior Publication Data

US 2001/0016032 A1 Aug. 23, 2001

(30) Foreign Application Priority Data

Feb. 18, 2000 (DE) .......................................... 100 07 601

(51) Int. Cl.[7] ................................................. H05G 1/64
(52) U.S. Cl. ............................... 378/15; 378/4; 378/19; 378/196; 378/197; 378/198
(58) Field of Search ................................ 378/4, 15, 19, 378/197, 198, 196; 343/771, 900

(56) References Cited

U.S. PATENT DOCUMENTS

| | | | | |
|---|---|---|---|---|
| 5,157,393 A | * | 10/1992 | Fox et al. | 340/870.3 |
| 5,579,357 A | * | 11/1996 | Harrison | 378/4 |
| 6,113,264 A | * | 9/2000 | Watanabe | 378/197 |
| 6,181,766 B1 | * | 1/2001 | Pearson, Jr. et al. | 378/15 |
| 6,301,324 B1 | * | 10/2001 | Pearson, Jr. et al. | 378/15 |

* cited by examiner

Primary Examiner—Robert H. Kim
Assistant Examiner—Allen C. Ho
(74) Attorney, Agent, or Firm—Schiff Hardin & Waite

(57) ABSTRACT

A medical device which has a data generating unit and a data processing unit that can be displaced relative to each other, as well as an arrangement for transferring the data from the data generating unit to the data processing unit. The arrangement for transferring the data includes a hollow conductor and an antenna that works in conjunction with the hollow conductor, which are displaced relative to each other in a defined manner in the displacement of the data generating unit and the data processing unit relative to each other, and via which the data transfer is accomplished.

10 Claims, 3 Drawing Sheets

MEDICAL DEVICE HAVING AN ARRANGEMENT FOR TRANSMITTING DATA FROM A DATA GENERATING UNIT TO A RELATIVELY DISPLACEABLE DATA PROCESSING UNIT

BACKGROUND OF THE INVENTION

1. Field of the Invention

The present invention relates to a medical device having data generating components forming a data generating unit and data processing components forming a data processing unit, the data generating unit and the data processing unit being displaceable relative to each other, as well as an arrangement for transferring data from the data generating unit to the data processing unit.

2. Description of the Prior Art

In many branches of technology, the problem has occasionally arisen that high volumes of data must be transferred from data generating unit to data processing unit, which can be displaced relative to each other. In medical technology, this problem exists in X-ray devices that have a C-arm that can be displaced relative to a device part.

Such an X-ray device is disclosed in German OS 197 46 096, corresponding to U.S. Pat. No. 6,079,876. The X-ray device is provided for generating 3D images from a series of 2D projections that are registered from various directions.

In C-arm radiography devices such as this, the image data that are acquired by an image pick-up unit that is arranged at the C-arm must be transferred to an image reproduction unit that is arranged in or at the device part. Conventionally, coaxial cable has been used for the transfer of data from the C-arm to the device part. Given an open cable guidance, this technique is easy to master. In contrast, the concealed cable guidance with cables that run in the C-arm and that can be wound and unwound on cable drums, as is described in German Patent 197 43 215, corresponding to U.S. Pat. No. 6,065,710, is more problematic. This is because suitable cable guidance for winding and unwinding the cable on the cable drums is required, as well as because the cable is subjected to many stressful bending events in procedures to displace the C-arm relative to the device part.

SUMMARY OF THE INVENTION

It is an object of the present invention to provide a medical device of the above described type wherein the transfer of data between data generating unit and data processing unit which are displaced relative to one another is simplified.

This object is inventively achieved in a medical device having a data generating unit and a data processing unit that can be displaced relative to each other, as well as an arrangement for transferring the data from the data generating unit to the data processing unit, wherein the unit for transferring the data has a hollow conductor and an antenna that operates in conjunction with the hollow conductor, which can be displaced relative to each other in a defined manner in the relative displacement of the data generating unit and the data processing unit. In a preferred embodiment of the invention, the hollow conductor is connected to the data generating unit, and the antenna is connected to the data processing unit. For the data transmission, the data which are generated by the data generating unit are modulated onto a carrier signal which, for medical applications, has a carrier frequency of 5.8 gigahertz, for example, and are coupled into the hollow conductor. The antenna, which is disposed in a defined manner relative to the hollow conductor, i.e. in a geometrically defined manner, receives the carrier signal, i.e. couples the carrier signal out of the hollow conductor, in a contact-free manner, so that after the carrier signal is demodulated the generated data are available to the data processing unit in their original form. The utilization of the hollow conductor and the antenna that is oriented relative to the hollow conductor, which can also be displaced relative to each other when the data generating unit and the data processing unit are displaced relative to each other, makes it possible to forgo transfer of the data by cable, and specifically avoids problems that are caused by the cable guidance and the winding and unwinding of cables in the displacement of two units that can be displaced relative to each other.

In a further preferred embodiment of the invention, the hollow conductor is provided with a slot along which or in which the antenna is guided in the displacement of the data generating unit and the data processing unit relative to each other. In this way, the antenna can couple the modulated carrier signal out of the hollow conductor with a high efficiency.

In the journal *Elektrotechnik* (73, Vol. 11, Nov. 23, 1991; 48–53), in an article by Uwe Bueltman entitled "Schlitz im Kleid", a data bus or rail is described which is provided for the contact-free transmission of data in automation technology and which has a slotted hollow conductor and an antenna which is guided in the slotted hollow conductor.

In another version of the invention the hollow conductor is provided with a perforation along which the antenna is guided in the displacement of the data generating unit and the data processing unit relative to each other. In this context, a perforation means an intentional thinning of the material of the hollow conductor or a series of local openings in the hollow conductor which is or are sufficient to enable electromagnetic waves that are conducted in the hollow conductor to exit the hollow conductor. The perforation can be constructed as a continuous perforation along the path of displacement of the antenna. The perforation likewise allows reception of the modulated carrier signal by the antenna and thus a contact-free transfer of data.

In a further embodiment of the invention, the data generating unit is an image pick-up unit, and the data processing unit is an image reproduction unit. The data that are generated by the data generating unit being transferred to the data processing unit in digital form in accordance with another variant. If the image pickup device generates analog data, the analog data are first converted into digital data by an analog/digital converter and then modulated with a carrier signal by a modulator. The modulated carrier signal is coupled into the hollow conductor on the image pick-up device side and is coupled out of the hollow conductor by the antenna on the image reproduction device side. Next, the modulated carder signal is fed to a demodulator for recovering the digital data and to a digital/analog converter for recovering the analog data. If the data are delivered by the image pick-up device in digital form, and the image reproduction device is able to process digital data, the analog/digital and digital/analog conversions can be omitted, In this way, given 16 bits of data, 30 images per second and a 1 $k^2$ image matrix (1000×1000 pixels), data volumes of 480 megabits per second and higher can be transferred from the image pick-up device to the image reproduction device.

In another embodiment of the invention for medical use of the device. The Invention is employed, for instance in a radiography device. This can be a radiography device with a C-arm that is mounted in a support of the radiography device such that it can be displaced along its circumference and that is provided with the image pick-up device. The hollow conductor extends along the circumference of the C-arm. The antenna can be disposed at the support of the C-arm. The antenna thus can be easily oriented in a defined manner relative to the hollow conductor. During displacements of the C-arm along its perimeter, the antenna, which is stationary relative to the hollow conductor, is guided either along or in the slot of the hollow conductor in accordance with one version of the invention, or along the perforation of the hollow conductor in accordance with the other version of the invention.

DESCRIPTION OF THE PREFERRED EMBODIMENTS

Figure 1:
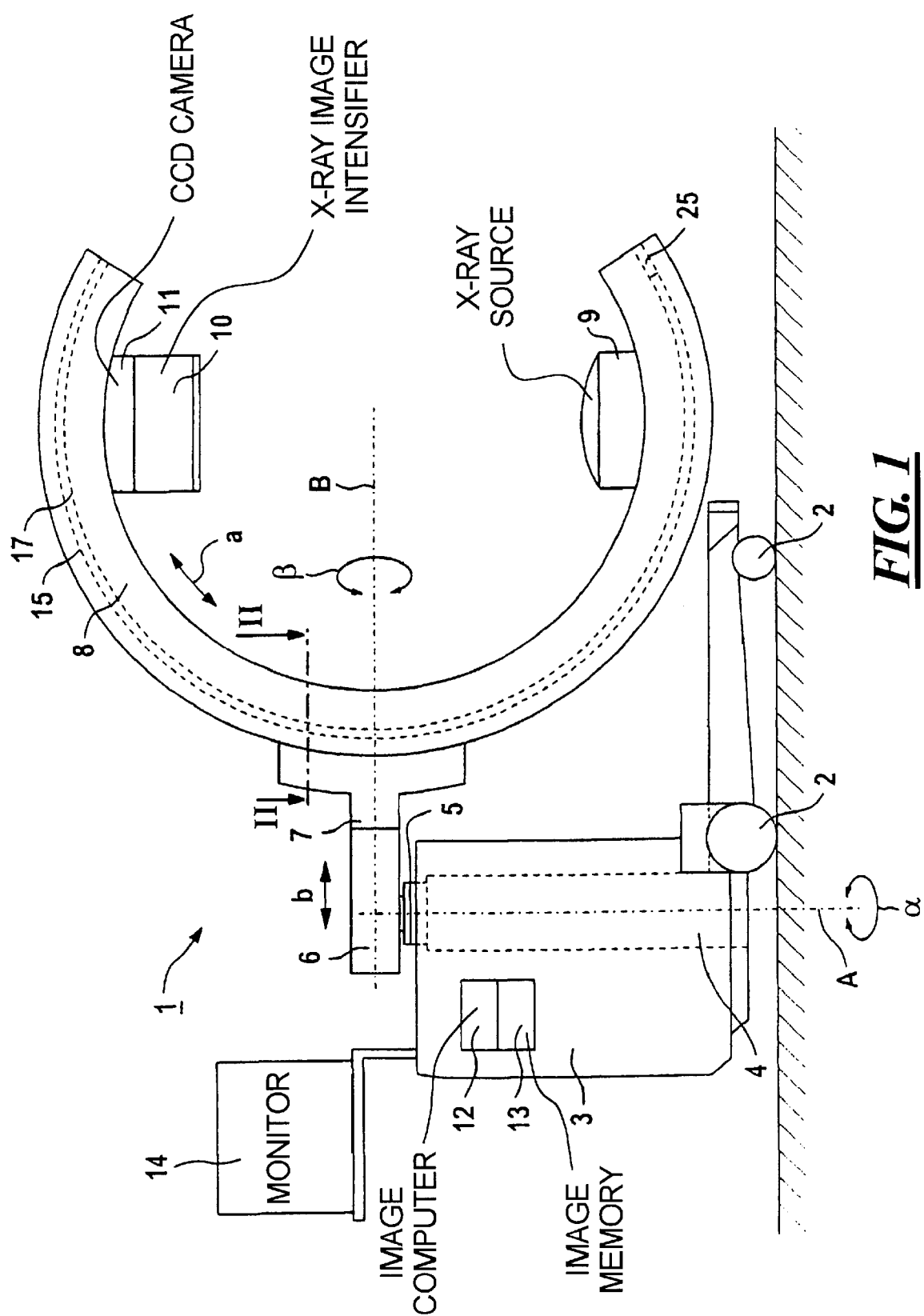
FIG. 1 shows an inventive device in the form of a C-arm radiography device.

FIG. 1 shows an inventive device in the form of a C-arm radiography device 1 having a device carriage 3 that can be moved on wheels 2. The C-arm radiography device 1 has a lifting device 4 (which is only schematically represented in FIG. 1) that has a column 5 with a longitudinal axle A around which the column 5 can be rotated in the directions of the double arrows α. At the column 5 a holder 6 is disposed, at which a support 7 for bearing a C-arm 8 is disposed. The support 7 is mounted at the holder 6 such that it can be rotated together with the C-arm 8 around a common axle B of the holder 6 and the support 7 in known fashion (double arrow β, angulation) and pushed in the direction of the axle B (double arrow b). The C-arm 8 is mounted such that it can be moved relative to the support 7 along its perimeter in the directions of the double arrow α (orbital motion). With the lifting device 4, the C-arm 8, which Is connected to the column 5 of the lifting device 4 via the support 7 and the holder 6, can be displaced vertically relative to the device carriage 3.

The C-arm 8 carries an X-ray source 9 and an oppositely mounted X-ray receiver, which is an X-ray image intensifier 10 in the exemplary embodiment. In the present exemplary embodiment, a CCD camera 11 which is allocated to the X-ray image amplifier 10 registers the X-ray images displayed on the output screen of the X-ray image amplifier 10. The image data are transferred to an image computer 12 and intermediately stored in an image memory 13 or are displayed on a monitor 14.

A hollow conductor 15 and an antenna 16 are provided for the contact-free transfer of the image data from the C-arm 8 that is provided with the CCD camera 11 to the support 7 which is connected to the device carriage 3 and is displaceable relative to the C-arm 8. The hollow conductor 15 is disposed along an outwardly facing peripheral surface 17 of the C-arm 8. As can be seen from FIG. 2, which shows a view in the direction of the arrows II from FIG. 1, the support 7, that is provided with rollers 16 for bearing the C-arm 8 has a recess 19, so that the hollow conductor 15 can move through the support 7 when the C-arm 8 is displaced relative to the support 7.

In the exemplary embodiment, the hollow conductor 15 is provided with a slot 20 which extends along the hollow conductor 15 and into which the antenna 16 that is disposed at the support 7 protrudes. The antenna 16 can be a dipole antenna. When the C-arm 8 is displaced relative to the support 7, the antenna 16 is guided in the slot 20 of the hollow conductor 15, accordingly. The hollow conductor 15 and the antenna 16 form a sub-path of the data communication path between the CCD camera 11 and the image computer 12, which is represented in FIG. 3 in a block diagram.

In the operation of the C-arm radiography device 1, the CCD camera 11 registers the X-ray images that are displayed on the output screen of the X-ray image amplifier 10, with the CCD camera 11 delivering parallel image data. These are converted into serial data by a converter 21, digitally converted in an analog-digital converter 22, and modulated by a modulator 23 onto a carrier signal that is generated by an oscillator 24, which has a carrier frequency of 5.8 gigahertz in the exemplary embodiment. The modulated carrier signal is coupled into the hollow conductor 15 that is disposed along the peripheral surface 17 of the C-arm 8, at the conductor end that is situated on the X-ray image amplifier side, with the other end terminating with an impedance 25 which is tuned to the carrier signal.

Figure 2:
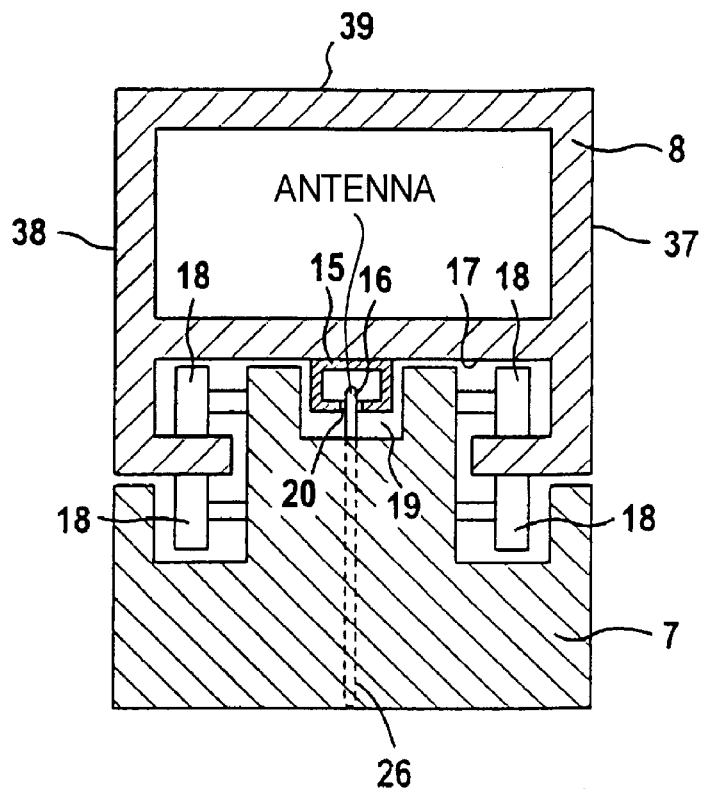
FIG. 2 is a view of a first communication path for the contact-free transfer of data in the direction of the arrows II from FIG. 1.
Figure 3:
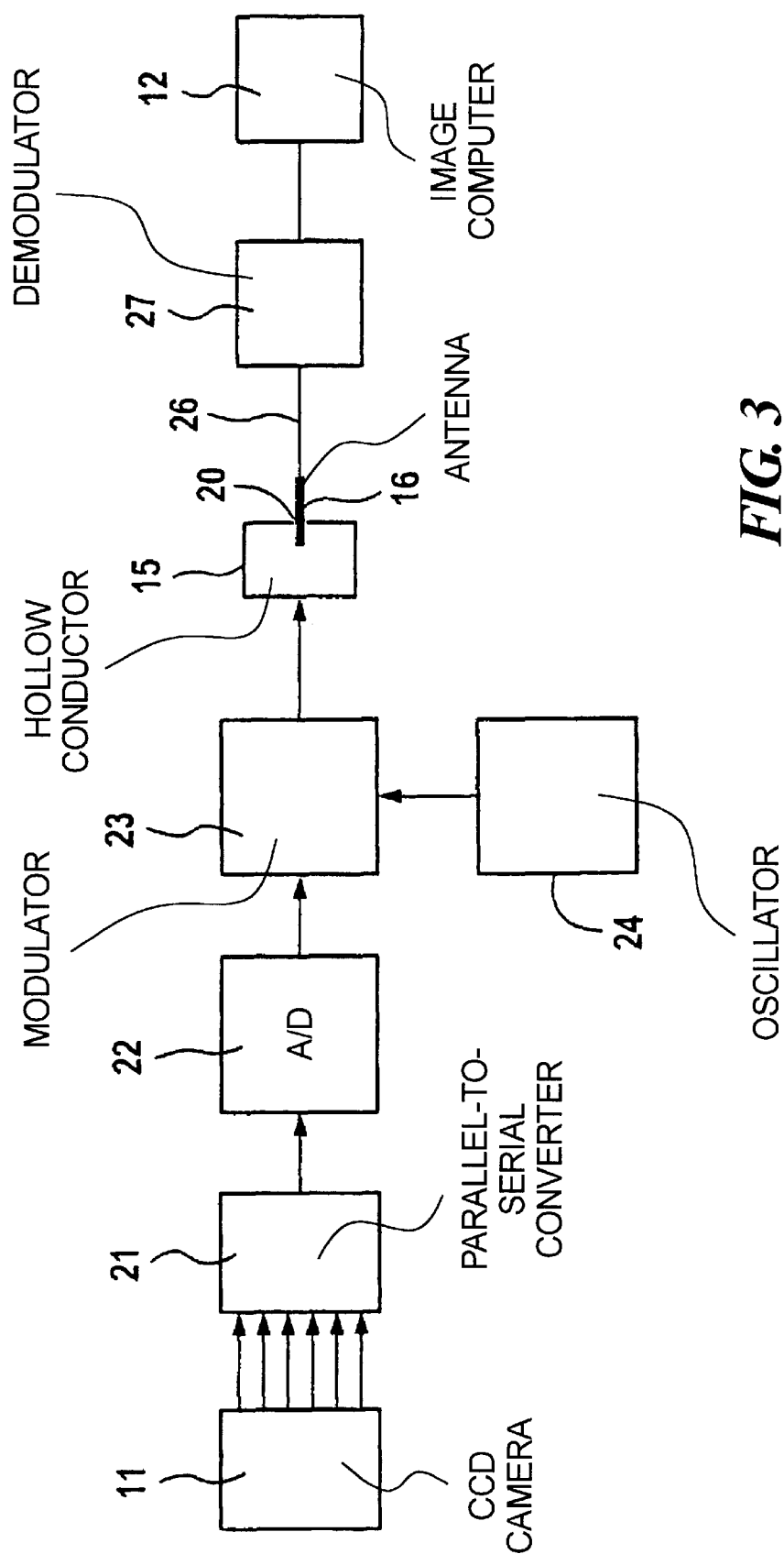
FIG. 3 is a block circuit diagram of the communication path between the data generating unit and the data processing unit in the inventive apparatus.

By means of the dipole antenna 16 that moves in the slot 20 of the hollow conductor 15, the modulated carrier signal is coupled from the hollow conductor 15 on the bearing side, said support 7 being stationary relative to the C-arm 8, and is connected to a demodulator 27 with a cable 26 that is schematically represented in FIG. 2 and FIG. 3. Now recovered, the digital image data are finally transferred to the image computer 12 that is disposed in the device carriage 3 of the C-arm radiography device 1, as described above. The image computer 12 temporarily stores the image data in the image memory 13 or may display the data on the monitor 14 of the C-arm radiography device 1.

Figure 4:
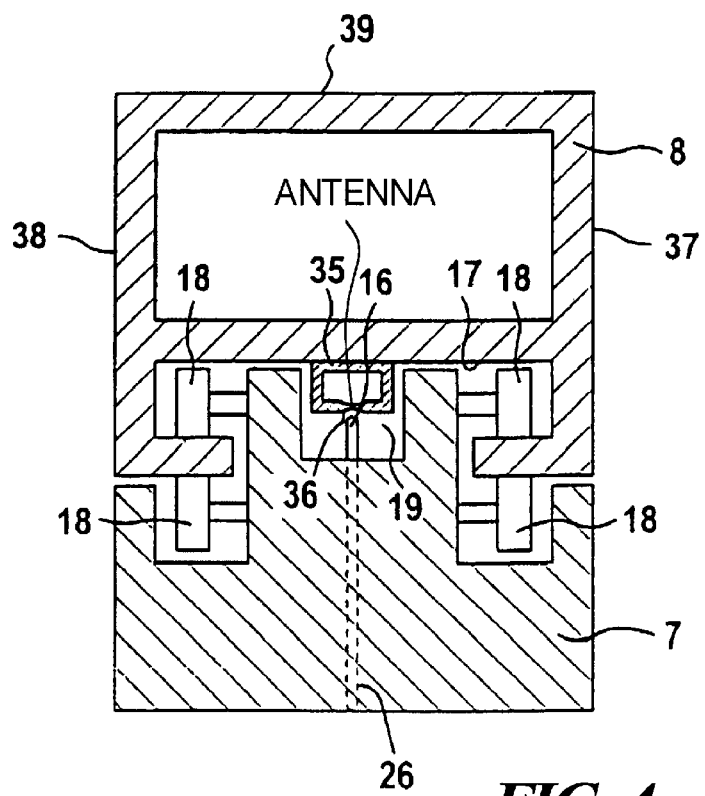
FIG. 4 is a view of a second embodiment of a communication path for the contact-free transfer of data in accordance with the invention.

FIG. 4 shows a second embodiment of a contact-free communication path. The view of FIG. 4 essentially corresponds to the view of FIG. 2; therefore, components that are represented in FIG. 4 that are at least substantially structurally and functionally identical to components that are represented in FIG. 2 are provided with the same reference characters. In contrast to the embodiment shown in FIG. 2, the hollow conductor 35 in FIG. 4 does not have a slot along its perimeter, but rather a perforation 36, which is constructed such that the modulated carrier signal can escape from the hollow conductor 35 at the perforation 36. The dipole antenna 16 is disposed at the support 7 in a definite manner relative to the perforation 36, so that in displacements of the C-arm 8 along its perimeter, the hollow conductor 35 with its perforation 36 moves in a defined manner relative to the dipole antenna 16. In this way, the antenna 16 can receive the modulated carrier signal exiting from the hollow conductor 35 at the perforation 36, and the modulated carrier signal can be fed to the image computer 12 in the manner described above.

In contrast to the described exemplary embodiments, the hollow conductors 15 and 35, respectively, need not be disposed at the C-arm 8 on the outwardly facing peripheral surface 17. Rather, the hollow conductor 15 and the hollow conductor 35 can be disposed at one of the side surfaces 37, 38 or, if expedient, at the inner peripheral surface 39 of the C-arm 8, it being necessary to adapt the arrangement and orientation of the dipole antenna 16 relative to the hollow conductor 15, 35 accordingly.

The invention has been described in the example of a medical device in the form of a C-arm radiography device. The application of the invention is not limited to radiography devices, however.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical device comprising:
   a data generating unit which generates data;
   a data processing unit, separate from said data generating unit, for processing said data;
   an arrangement for producing relative displacement between said data processing unit and said data generating unit; and
   an arrangement for transmitting said data from said data generating unit to said data processing unit during said relative displacement, comprising an antenna and a hollow conductor for producing a wireless communication path between said data processing unit and said data generating unit, said antenna and said hollow conductor being displaced relative to each other in a defined manner in conjunction with said relative displacement of said data processing unit and said data generating unit.

2. A medical device as claimed in claim 1 wherein said hollow conductor is connected to said data generating unit and wherein said antenna is connected to said data processing unit.

3. A medical device as claimed in claim 1 wherein said hollow conductor has a slot therein along which said antenna is guided during said relative displacement of said data generating unit and said data processing unit.

4. A medical device as claimed in claim 1 wherein said hollow conductor has a slot therein in which said antenna is guided during said relative displacement of said data generating unit and said data processing unit.

5. A medical device as claimed in claim 1 wherein said hollow conductor has a perforation along which said antenna is guided during said relative displacement of said data generating unit and said data processing unit.

6. A medical device as claimed in claim 1 wherein said data generating unit comprises an image pick-up device for picking up image data, and wherein said data processing unit comprises an image reproduction device for reproducing an image corresponding to said image data.

7. A medical device as claimed in claim 1 wherein said data generating unit emits said data in digital form, and wherein said data transfer arrangement transfers said data in digital form to said data processing unit.

8. A medical device as claimed in claim 1 wherein said data generating unit comprises a unit for obtaining radiography data as said data, and wherein said data processing unit comprises a unit for producing a radiographic image from said radiographic data.

9. A medical device as claimed in claim 8 wherein said data generating unit comprises a C-arm having a radiation source and a radiation receiver mounted thereon, said hollow conductor being disposed along a circumferential perimeter of said C-arm, said C-arm having a C-arm support, in which said C-arm is displaceably received for allowing movement of said C-arm along said circumferential perimeter.

10. A medical device as claimed in claim 8 wherein said antenna is disposed at said C-arm support.

* * * * *